United States Patent
Brockway et al.

(10) Patent No.: US 7,529,583 B1
(45) Date of Patent: May 5, 2009

(54) THERAPEUTIC DEVICE AND METHOD USING FEEDBACK FROM IMPLANTABLE PRESSURE SENSOR

(75) Inventors: Brian P. Brockway, Shoreview, MN (US); Brian D. Pederson, Andover, MN (US); David G. Benditt, Edina, MN (US)

(73) Assignee: Transoma Medical, Inc., St. Paul, MN (US)

( * ) Notice: Subject to any disclaimer, the term of this patent is extended or adjusted under 35 U.S.C. 154(b) by 266 days.

(21) Appl. No.: 10/756,188

(22) Filed: Jan. 12, 2004

Related U.S. Application Data

(60) Provisional application No. 60/440,151, filed on Jan. 15, 2003.

(51) Int. Cl.
 *A61N 1/39* (2006.01)
(52) U.S. Cl. .............................. 607/6; 607/23; 600/515
(58) Field of Classification Search .................. 607/6, 607/9, 14, 17, 22, 23, 62, 63
 See application file for complete search history.

(56) References Cited

U.S. PATENT DOCUMENTS

| | | | |
|---|---|---|---|
| 3,805,795 A * | 4/1974 | Denniston et al. ............... | 607/6 |
| 4,114,628 A * | 9/1978 | Rizk ............................... | 607/4 |
| 4,291,699 A * | 9/1981 | Geddes et al. .................. | 607/6 |
| 4,774,950 A | 10/1988 | Cohen | |
| 4,846,191 A | 7/1989 | Brockway et al. | |
| 5,269,301 A | 12/1993 | Cohen | |
| 5,431,685 A | 7/1995 | Alt | |
| 5,480,412 A * | 1/1996 | Mouchawar et al. ........... | 607/6 |
| 5,487,760 A | 1/1996 | Villafana | |
| 5,865,749 A | 2/1999 | Doten et al. | |
| 6,033,366 A | 3/2000 | Brockway et al. | |
| 6,259,936 B1 | 7/2001 | Boggett et al. | |
| 6,477,406 B1 | 11/2002 | Turcott | |
| 6,480,733 B1 | 11/2002 | Turcott | |
| 6,491,639 B1 | 12/2002 | Turcott | |
| 6,527,729 B1 | 3/2003 | Turcott | |
| 6,561,948 B2 | 5/2003 | Markyvech et al. | |
| 6,575,912 B1 | 6/2003 | Turcott | |
| 6,600,949 B1 | 7/2003 | Turcott | |
| 6,937,899 B2 * | 8/2005 | Sheldon et al. ................ | 607/18 |
| 2002/0072731 A1 | 6/2002 | Doten et al. | |
| 2002/0107559 A1 | 8/2002 | Sanders et al. | |

\* cited by examiner

*Primary Examiner*—Kennedy J Schaetzle
(74) *Attorney, Agent, or Firm*—Fish & Richardson P.C.

(57) ABSTRACT

Devices and methods to reduce the incidence of both false positive and false negative detection of rhythm anomalies. Implantable devices that measure vascular pressure, vascular blood flow, tissue perfusion, and/or intracardial pressure provide feedback directly to the therapeutic device to improve aberrant rhythm detection.

23 Claims, 6 Drawing Sheets

US 7,529,583 B1

THERAPEUTIC DEVICE AND METHOD USING FEEDBACK FROM IMPLANTABLE PRESSURE SENSOR

CROSS-REFERENCES TO RELATED APPLICATIONS

This application relates to and claims the benefit of U.S. Provisional Patent Application No. 60/440,151, filed Jan. 15, 2003, the entire disclosure of which is incorporated herein by reference.

BACKGROUND OF THE INVENTION

The present invention generally relates to implantable therapeutic devices such as implantable cardioverter defibrillators that deliver therapy as a function of feedback from an implanted sensor.

Most commercially available implantable cardioverter defibrillators analyze electrocardiogram (ECG) signals to determine when to apply a stimulus to the heart to correct an aberrant rhythm. Even when the ECG is measured from the endocardium and is therefore relatively free of artifact, detection algorithms fail to perform perfectly, as evidenced by Wilkoff et. al. [Critical Analysis of Dual-Chamber implantable Cardioverter-Defibrillator Arrhythmia Detection, B L Wilkoff, et. al. Circ. 2001: 103: 381-386]

Considerable prior work and thought has been given to using hemodynamic measurements to improve detection. For example, in U.S. Pat. No. 4,774,950 to Cohen, the use of various hemodynamic measurements are proposed to improve the ability to detect $V_{fib}$ and $V_{tach}$. Hemodynamic measurements previously considered viable include heart rate, stroke volume, cardiac output, blood flow and endocardial venous pressures as well as blood flow. See for example U.S. Pat. No. 5,431,685 to Alt. Much of the work in this area has been focused on the use of endocardial pressure or heart wall activity measurements, such as those obtained from the venous pressure sensing lead used on the Chronicle™"manufactured by Medtronic in Fridley, Minn. The Chronicle™"" device and method of use may be the most well developed of these techniques and involves directing a lead containing a distal pressure sensor through venous system and into the right side of the heart. However, this approach is disadvantageous because the lead occupies space within the vein that may already contain multiple endocardial leads that are used for pacing and/or defibrillation. In addition, a lead placed in the heart is subject to significant motion from the beating heart and is therefore a challenge to achieving high reliability, especially for those patients that have a long life expectancy.

BRIEF SUMMARY OF THE INVENTION

The devices and methods of the present invention may be used, by way of example, not limitation, to reduce the incidence of both false positive and false negative detection of rhythm anomalies. For example, the devices and methods of the present invention may be used to better detect an abnormal potentially life threatening heart rhythm, such that implantable therapeutic devices such as implantable cardioverter defibrillators are less likely to deliver a potentially painful or uncomfortable stimulus when it is not needed, and less likely to fail to deliver a stimulus when it is necessary to save the patient's life. The devices and methods of the present invention may be implanted in the patient to measure vascular pressure, vascular blood flow, tissue perfusion, and/or intracardial pressure, and may provide direct feedback to the implantable therapeutic devices to improve aberrant rhythm detection.

DETAILED DESCRIPTION OF THE INVENTION

The following detailed description should be read with reference to the drawings in which similar elements in different drawings are numbered the same. The drawings, which are not necessarily to scale; depict illustrative embodiments and are not intended to limit the scope of the invention.

Figure 10:
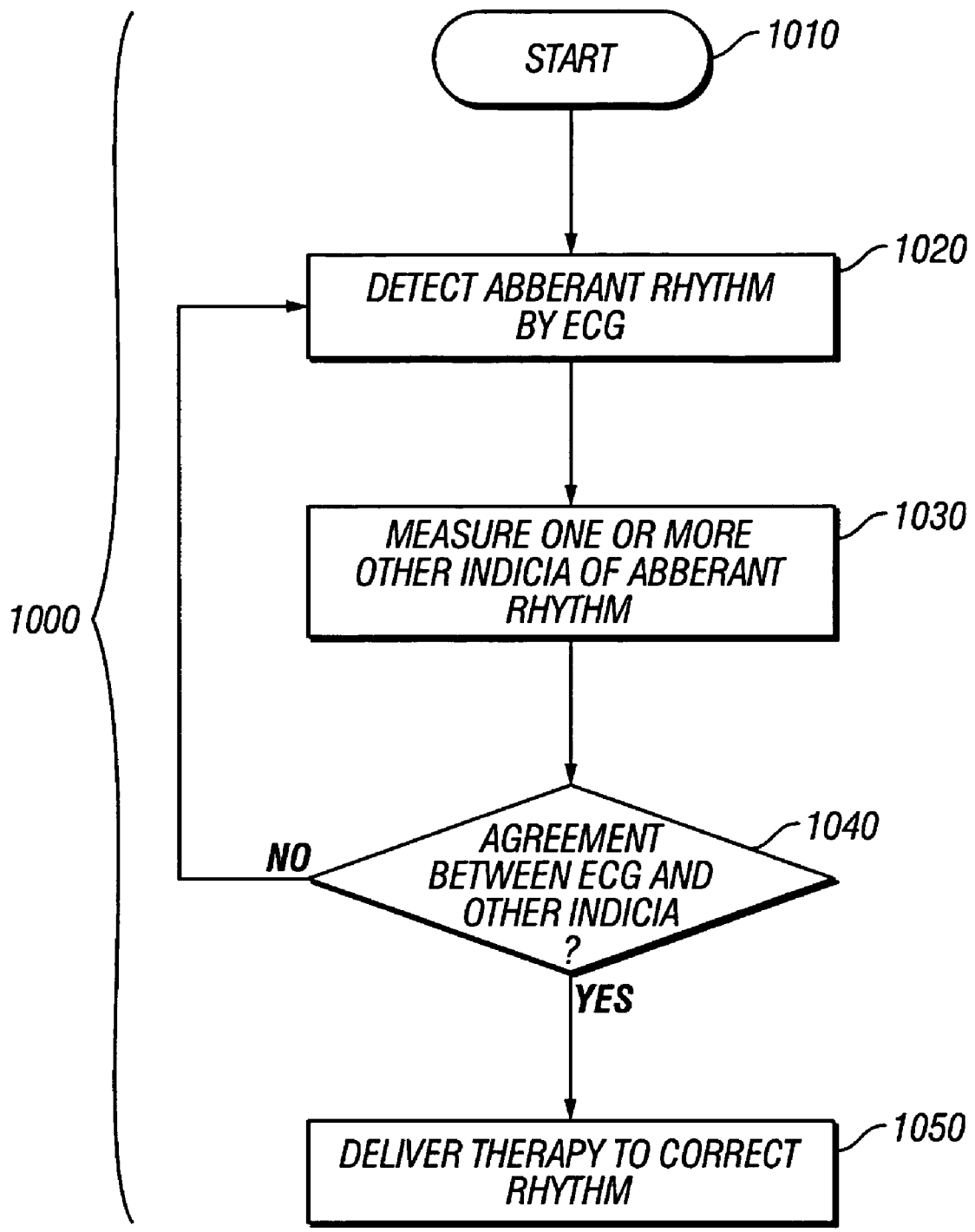
FIG. 10 is a block diagram illustrating a method of using sensor feedback to gate therapy delivery.

The various sensors disclosed herein may be used to gate or otherwise confirm/disconfirm a primary feedback parameter to control an implantable therapy device (ITD). For example, an ITD may use an electrocardiogram (ECG) as a primary feedback parameter to detect an aberrant heart rhythm in order to trigger the delivery of therapy to correct the aberrant rhythm. Because the primary feedback parameter may not always be an infallible indicator of an aberrant rhythm, an implantable sensor device (ISD) may be used to measure another indicator to confirm or disconfirm the presence of an aberrant heart rhythm before therapy is delivered. Such a method 1000 is schematically illustrated in FIG. 10 and is applicable to all sensor devices and systems disclosed herein. Initially 1010, an aberrant heart rhythm is detected by measuring 1020 a primary feedback parameter such as ECG. At or about the same time, a secondary feedback parameter indicative of an aberrant heart rhythm may be measured 1030. The primary feedback parameter may be compared 1040 to the secondary feedback parameter to determine if there is agreement or disagreement between the indicia.

If there is agreement between the measured parameters/indicia, the likelihood of a false positive or false negative is reduced. If both the primary indicator and the secondary indicator are in agreement as to the existence of an aberrant heart rhythm, then therapy may be delivered 1050. If there is not agreement, or if both the primary indicator and the secondary indicator are in agreement as to the nonexistence of an aberrant heart rhythm, therapy may be (at least initially) bypassed and the loop 1020/1030-1040 may be repeated. In this manner, the therapy is not inadvertently delivered when the primary feedback parameter erroneously indicates an aberrant heart rhythm. This method may be implemented in the form of an algorithm executable by electronics contained in the ITD or the ISD, for example.

Figure 1:
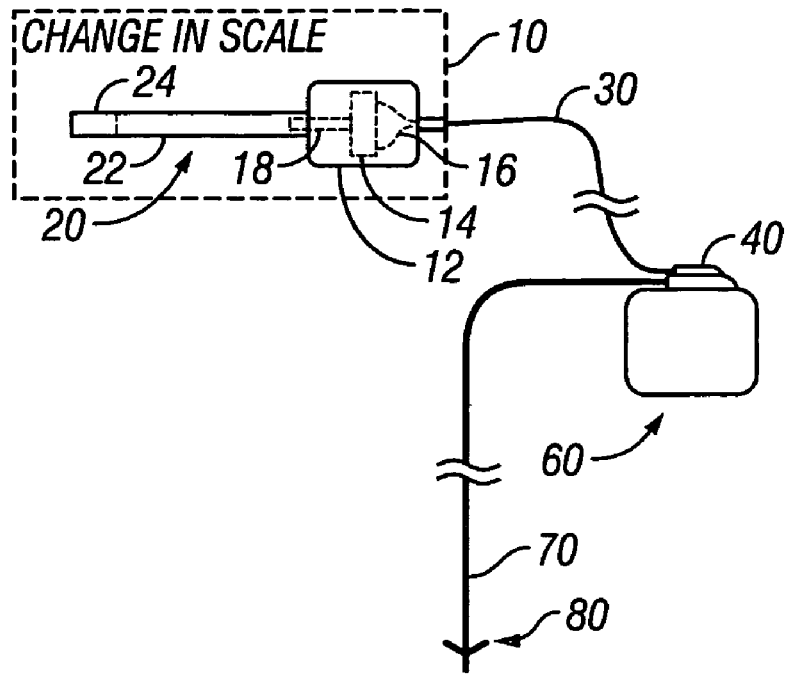
FIG. 1 is a schematic illustration of an implantable pressure sensing device combined with an implantable therapeutic device, shown in the form of an implantable cardioverter defibrillator.

With reference to FIG. 1, an implantable pressure sensing device (PSD) 10 and an implantable therapeutic device (ITD) 60 are shown. By way of example, not limitation, the ITD 60 is shown in the form of an implantable cardioverter defibrillator (ICD). The ITD 60 may comprise other therapeutic devices that correct aberrant heart rhythms, such as a drug infusion pump or a pacemaker. The following disclosure is given with specific reference to an ICD, but is understood to be equally applicable to other ITDs.

The PSD 10 is connected to the ICD 60 by an electrical lead 30. PSD 10 measures blood pressure and generates an electrical pressure signal which is transmitted in analog or digital form to the ICD 60 via lead 30. The lead 30 is preferably flexible, and may be similar to conventional pacing leads. A releasable connector 40 may be provided on the ICD 60 to facilitate easy connection and disconnection of the lead 30. This provides the physician with flexibility during placement of the lead 30 and PSD 10 as well as replacement of the PSD 10 at a later time should it fail or when the battery depletes.

The ICD 60 may otherwise be substantially conventional, with the exception of suitable signal processing electronics to receive and analyze (e.g., by a suitable algorithm) the pressure signal generated by the PSD 10. The ICD 60 may utilize a conventional endocardial lead 70 with a distal endocardial electrode 80 (as shown) to deliver the desired therapeutic electrical stimulus. Alternatively, subcutaneous (i.e., nonendocardial) electrodes may be used, such as those described in U.S. Patent Application Publication No. 2002/0107559 to Sanders et al., assigned to Cameron Health, the entire disclosure of which is incorporated herein by reference.

Figure 2:
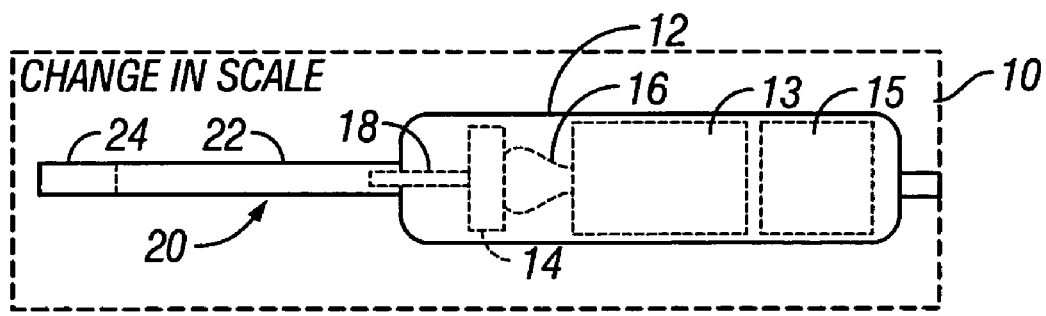
FIG. 2 is a schematic illustration of an alternative implantable pressure sensing device.

The PSD 10 includes a hermetically sealed housing 12 containing a pressure transducer 14 that converts fluidic pressure measurements or signals into electrical signals. The transducer 14 may be directly coupled by a plurality of wires 16 to lead 30 which transmits the electrical signals to the ICD 60, which provides the necessary signal processing and power supply functions. Alternatively, as seen in FIG. 2, the PSD 10 may provide these functions by containing within housing 12 an electronics module 13 and battery 15 for signal processing and power functions, respectively. These features are described in more detail in U.S. Pat. No. 6,033,366, to Brockway et al., the entire disclosure of which is incorporated herein by reference.

The PSD 10 also includes a pressure transmission catheter 20. The PTC 20 has a proximal end connected to the housing 12 and a distal end sized for insertion into a vascular lumen. The PTC 20 also includes a lumen in fluid communication with the pressure transducer contained in the housing 12. The lumen of the PTC 20 may be filled with a viscous fluid 22, with a distally disposed barrier 24 (e.g., gel plug or ePTFE membrane) that readily transmits pressure signals, but otherwise retains the fluid in the lumen of the PTC 20. Further aspects of the PTC 20 are disclosed in U.S. Pat. No. 4,846,191 to Brockway et al., the entire disclosure of which is incorporated herein by reference.

A significant benefit of the PTC 20 for measurement of pressure in a vascular lumen is that the size of the PTC 20 may be quite small. For example, the PTC 20 may be approximately 0.5 mm-1.5 mm diameter, which is substantially smaller than the 3.5 mm diameter pressure-sensing catheter used on the Chronicle™ device. In addition to a much smaller diameter, the portion of the PTC 20 that is inserted into the artery to assure a stable placement and obtain accurate pressure measurements is only about 5 mm to 10 mm, thus allowing the PTC 20 to be relatively short. One benefit of small size is that there is a much lower surface area of the sensor exposed to the blood. The smaller the surface area (all other factors such as material properties being equal) the lesser the risk of thromboembolism. A further benefit of smaller size is that the risk of hematoma is reduced (a small puncture in the vessel wall is more likely to seal tightly than is a larger hole). The smaller and lighter PSD 10 is more easily inserted (a small introducer can be used that results in significantly less bleeding during insertion and the need for extended application of pressure to stop bleed after introduction is greatly reduced), and is less likely to damage the endothelial surface (because lower mass and size is less likely to cause trauma if it bumps into the vessel wall as a result of blood flow eddies and changes in patient posture).

The PSD 10 and/or the ICD may optionally include ECG electrodes for measuring ECG signals. For example, electrodes may be incorporated on the housing of the ICD 60, on the electrode lead 70 of the ICD 60, on the interconnect lead 30 between the PSD 10 and ICD 60, on the housing 12 of the PSD 10, and/or on the PTC 20 of the PSD 10. Such ECG electrodes may be electrically coupled to the signal processing circuitry of the ICD 60.

With reference to FIG. 2, the PSD 10 and the ICD 60 are shown implanted in a patient 100. The ICD 60 is implanted in a conventional manner with the lead 70 extending endocardially through the superior vena cava 112, through the right atrium 114, with the electrode 80 residing in the right ventricle 116 as shown. Alternatively, the electrode may reside in the right atrium 114. As mentioned before, non-endocardial electrode placement may also be used, such as subcutaneous placement.

The PSD 10 is implanted in the patient 100 with at least the distal end of the PTC 20 disposed in a vascular lumen, such as the subclavian artery 118, while the housing 12 of the PSD 10 remains outside the subject vascular lumen. The relatively small diameter and short length of the PTC 20 has minimal impact on blood flow. Arterial placement of the PTC 20 may be preferred over venous placement since the superior vena cava 112 already contains lead 70, and additional obstructions may compromise blood flow. Even if the lead 70 of the ICD 60 did not occupy a venous lumen such as the superior vena cava 112, it is conventional to use a venous approach for other diagnostic and therapeutic devices, and placing the PTC 20 in an arterial site leaves such a venous approach available. Further, arterial blood pressure is a preferred measure of cardiac function.

Although the PTC 20 is shown disposed in the subclavian artery 118, those skilled in the art will recognize that other non-endocardial or peripheral vascular sites are also possible, such as the pulmonary artery, brachial artery or the femoral artery, for example. Furthermore, although the PSD 10 provides significant benefit for detecting rhythm disturbances when used to measure pressures in non-endocardial sites (e.g., peripheral artery), the PSD 10 may also be effectively used in this application for measuring endocardial pressure in any chamber of the heart 110. An example of this latter approach is described with reference to FIGS. 8 and 9.

To determine if an aberrant rhythm has developed in the patient's heart 110, the signal processing circuitry of the ICD 60 evaluates the pressure signal generated by the PSD 10, either alone or in combination with an ECG signal. Signal processing circuitry known to those skilled in the art may be used to detect aberrant rhythms as a trigger for stimulus. Preferably, ECG and pressure are evaluated independently.

A function (e.g., algorithm) for both the pressure and ECG signals may be used to indicate the likelihood that an aberrant rhythm requiring a stimulus is occurring in the heart 110. The algorithm would deliver a stimulus if the likelihood function derived from either signal indicated a very high degree of certainty that a stimulus was needed. If the likelihood function of a given signal indicated a lesser degree of certainty that a stimulus was needed, then the likelihood function of the other signal would be evaluated and the resulting composite likelihood function would be used to determine if a stimulus was needed. The likelihood functions may be designed to be dependent on signal quality. For example, if the ECG signal was extremely noisy and difficult to interpret, the likelihood function would present a low likelihood that an aberrant rhythm was present, even if other factors of the analysis indicated that such a rhythm was present.

Detection of the presence of an aberrant rhythm from the hemodynamic (pressure) signal may be accomplished in several ways. A baseline measurement of pressure may be established and if pressure fell by more than a pre-specified value from the baseline measurement, detection of an aberrant rhythm would occur. Alternately, detection would occur if actual pressure fell below a pre-specified value, such as a mean pressure below 50 mmHg or a systolic pressure below 60 mmHg. Alternately, the ICD 60 would differentiate the signal. If the differential exceeded a pre-specified negative value, detection of an aberrant rhythm would be signaled. A likelihood function would be generated dependent upon the specific characteristics of the differential.

Figure 3:
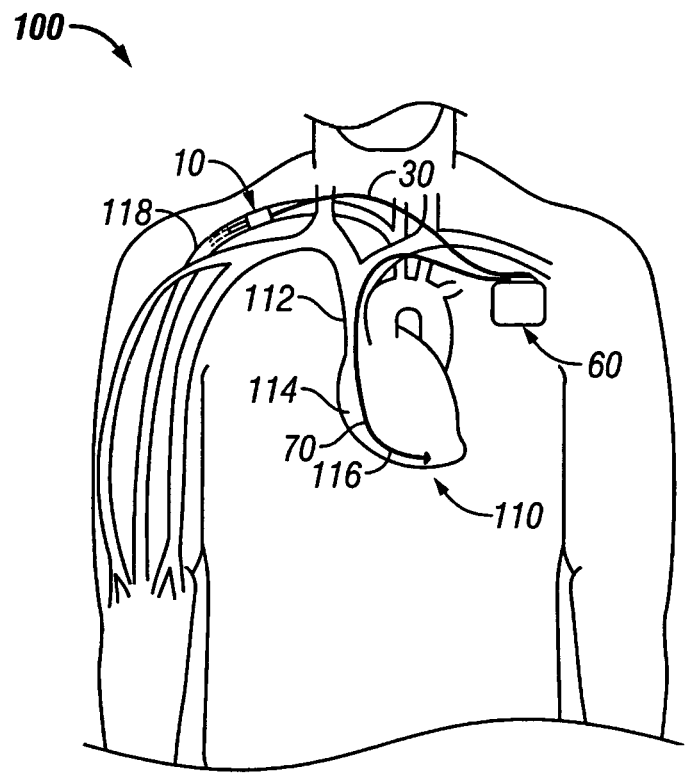
FIG. 3 is a schematic illustration of the pressure sensing device and implantable cardioverter defibrillator of FIG. 1 shown implanted in a patient.
Figure 4:
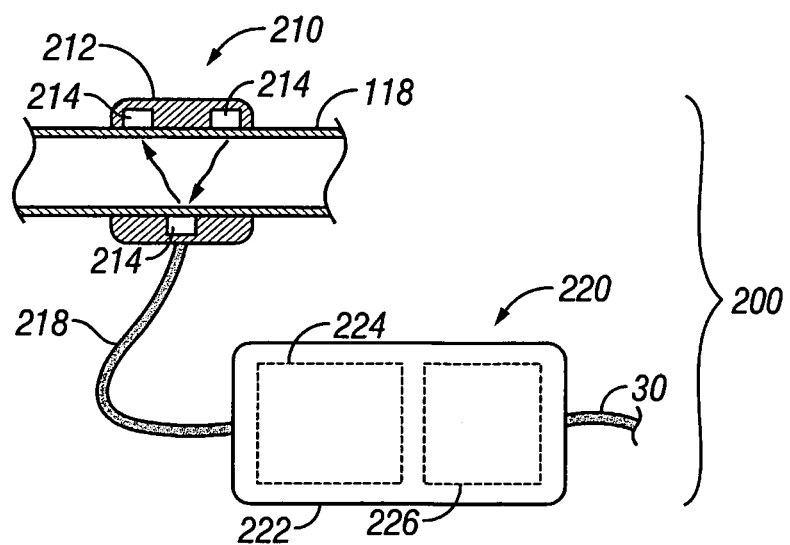
FIG. 4 is a schematic illustration of a flow sensing device that may be used in place of the pressure sensing device illustrated in FIGS. 1 and 2.
Figure 5:
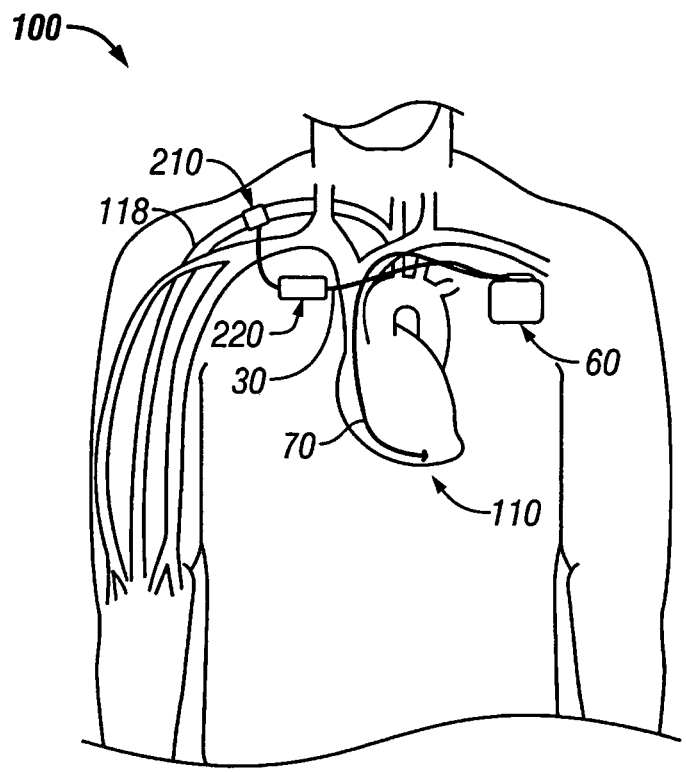
FIG. 5 is a schematic illustration of the flow sensing device of FIG. 4 and an implantable cardioverter defibrillator shown implanted in a patient.

With reference to FIGS. 4 and 5, a flow sensing device (FSD) 200 may be used in place of the PSD 10 described with reference to FIGS. 1-3. In this alternative embodiment, the FSD 200 measures blood flow rate and generates an electrical flow signal which is transmitted in analog or digital form to the ICD 60 via lead 30. The flow measurement signal is indicative of $V_{fib}$ and/or $V_{tach}$. A relatively rapid reduction in flow (or velocity) in a peripheral artery (such as the subclavian artery 118) will occur for reasons similar to those that result in a reduction in pressure during rhythm disturbances that require a therapeutic stimulus to the heart. Thus, the flow measurement provided by FSD 200 may be used as a surrogate for the pressure measurement provided by PSD 10 described previously.

FSD 200 includes a transducer cuff assembly 210 and an electronics assembly 220. Cuff assembly 210 includes a housing 212 sized and shaped to fit around a blood vessel, such as subclavian artery 118. Cuff housing 212 may be formed of a moldable biocompatible polymer, for example, and may have an adjustable size to accommodate vessels of different diameters. An example of a suitable cuff design is disclosed in U.S. Patent Application Publication No. 2002/0072731 to Doten et al., the entire disclosure of which is incorporated by reference.

A plurality of transducers 214 are disposed in the housing 212 at diametrically opposite positions to facilitate flow measurement within the vascular lumen. The transducers 214 may be ultrasonic transducers, for example, and blood flow may be measured by continuous wave Doppler, pulsed Doppler, or transit time techniques, for example. Other flow measurement techniques such as thermal dilution maybe used as well. The transducers 214 of the cuff assembly 210 maybe connected to a separate electronics assembly 220 by lead 218. Electronics assembly 220 includes a hermetically sealed housing 222 containing a suitable signal processing circuit 224 and battery power source 226. An example of a suitable transducer arrangement and electronics assembly is described in U.S. Pat. No. 5,865,749 to Doten et al., the entire disclosure of which is incorporated herein by reference.

Figure 6:
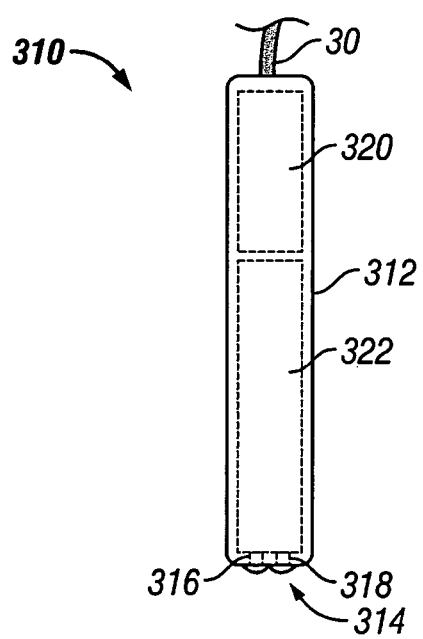
FIG. 6 is a schematic illustration of a tissue perfusion monitor that may be used in place of the pressure sensing device illustrated in FIGS. 1 and 2.
Figure 7:
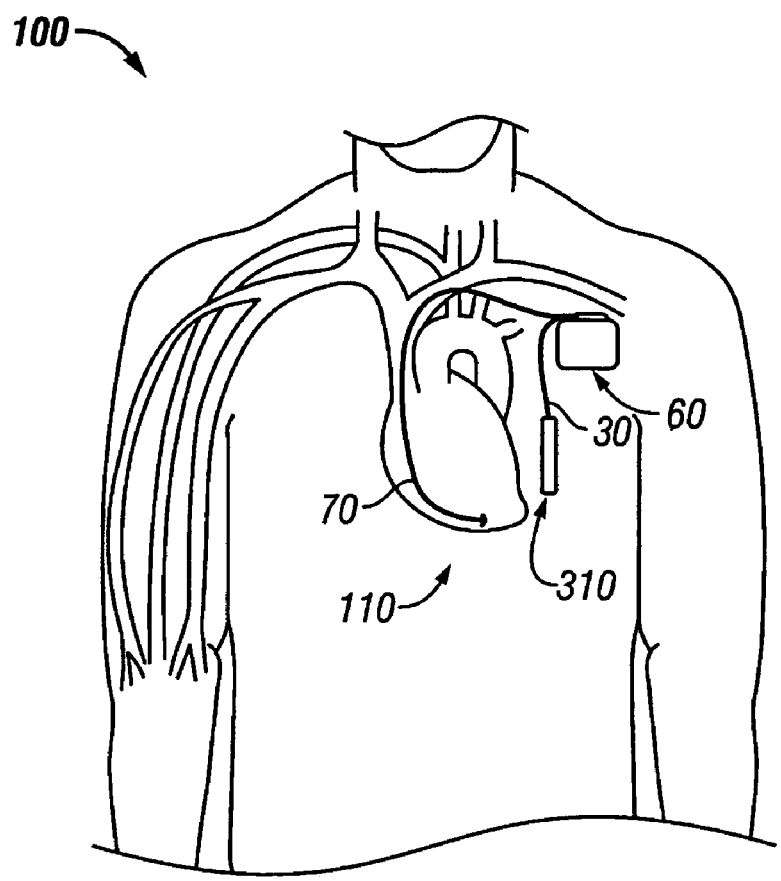
FIG. 7 is a schematic illustration of the tissue perfusion monitor of FIG. 6 and an implantable cardioverter defibrillator shown implanted in a patient.

With reference to FIGS. 6 and 7, a tissue perfusion monitor (TPM) 310 may be used in place of the PSD 10 described previously. In this alternative embodiment, the TPM 310 measures blood perfusion in tissue and generates a blood perfusion signal which is transmitted in analog or digital form to the ICD 60 via lead 30. The degree of tissue perfusion is highly dependent upon arterial pressure, and tissue perfusion drops noticeably within a few seconds following a drop in pressure in the artery delivering blood to the tissue being monitored. Therefore, the blood perfusion signal generated by TPM 310 may be used as an indicator of $V_{fib}$ and/or $V_{tach}$. By monitoring tissue perfusion frequently (e.g. several times per second to once every few seconds) an event that has resulted in a sudden drop in arterial pressure (such as $V_{fib}$ or $V_{tach}$) may be detected. The degree of tissue perfusion as measured by TPM 310 may be used in a manner similar to how hemodynamic measurements can be used to provide a more effective therapy, either alone or in combination with other information such as ECG and pressure. Thus, the flow measurement provided by FSD 200 may be used together with or as a surrogate for the pressure measurement provided by PSD 10 described previously.

The TPM 310 may utilize, for example, laser Doppler techniques to measure blood perfusion in tissue. As seen in FIG. 6, the TPM 310 includes a hermetically sealed housing 312 containing a source of coherent light (e.g., laser) 316 and one or more photodetectors 318 with associated collecting lenses 314 which interface with the tissue to be monitored. For purposes of the clinical applications discussed herein, any well vascularized tissue may be monitored at a convenient in-vivo site such as adjacent the ICD 60 as shown in FIG. 7. The photodetectors 318 are connected to suitable signal processing circuitry 322 powered by battery 320. Examples of suitable laser Doppler componentry may be found in U.S. Pat. No. 6,259,936 to Boggett et al. and European Patent Application No. 0282210AI to Fujii.

A benefit of the TPM 310 is that it does not require insertion into an artery or cardiac chamber. Another benefit is that the TPM 310 may be incorporated as an integral part of the ICD 60, with the lenses extending through the housing and the light emitter/detector and electronics disposed inside the housing, thus eliminating the need for additional leads. This would have particular benefit for use with subcutaneously implanted defibrillators, since it is an objective of such devices to eliminate the use of any leads.

Figure 8:
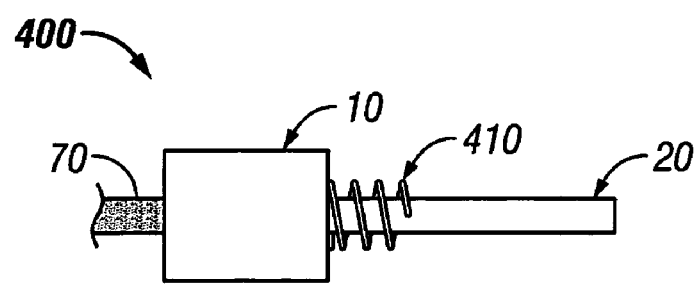
FIG. 8 is a schematic illustration of an implantable pressure sensing device including an anchoring electrode, and an implantable therapeutic device, shown in the form of an implantable cardioverter defibrillator or pacemaker.
Figure 9:
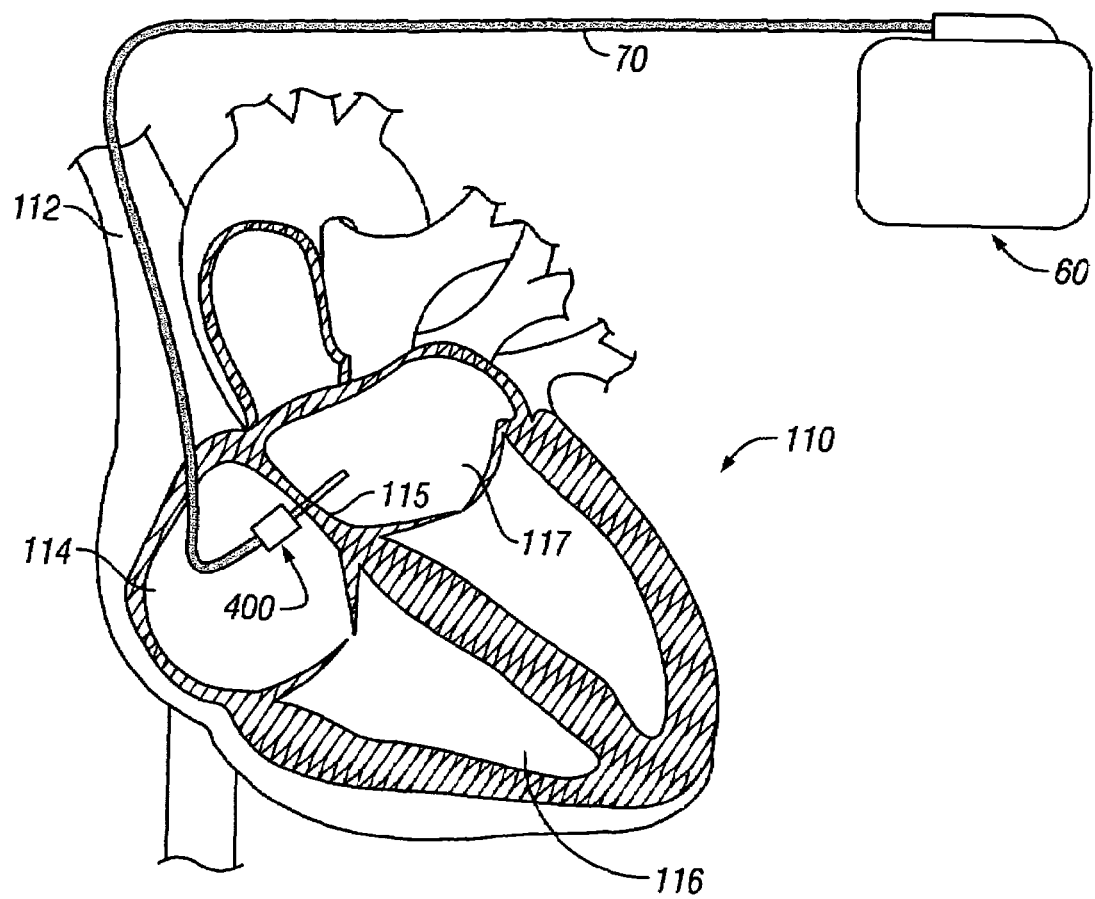
FIG. 9 is a schematic illustration of the pressure sensing device and anchoring electrode of FIG. 8 shown implanted across a patient's atrial septal wall.

With reference to FIGS. 8 and 9, a combined pressure sensing and electrode device (PSED) 400 is shown. The PSED 400 generally includes a PSD 10 as described previously, in addition to an anchoring electrode 410, which facilitates both as a stimulus electrode for pacing or defibrillation purposes, and as an anchor to hold the PSD 10 to the atrial septal wall 115 with the PTC 20 extending across the septal wall 115 and into the left atrium 117. The PSED 400 in conjunction with the ITD 60 allows for both the delivery of therapeutic stimulus (e.g., pacing or defibrillation) via electrode 410 to the intra-atrial septum 115 and the measurement of pressure in the left atrium 117 for feedback and triggering purposes, for example. The PSED 400 may be placed at any convenient location on the right atrial side of the septum 115, but preferably where there is sufficient viable tissue for anchoring and conduction purposes to achieve appropriate pacing and pressure measurement thresholds. For example, the PSED 400 may be positioned in the area of Bachmann's bundle, which is a fast conduction pathway to the left atrium 117 know to quickly depolarize the chambers of the heart 110.

The PSED 400 may be implanted on the right side of the atrial septum with the PTC 20 extending into the left atrium, or the PSED 400 may be implanted on the epicardium adjacent the left ventricle with the PTC 20 extending across the left ventricular free wall into the left ventricle. To obtain the epicardial position, the PSED 400 may be implanted using a delivery tube and a pericardial access device inserted via a subzyphoid approach.

To obtain the transeptal position as shown in FIG. 9, the PSED may be initially delivered to the right atrium 114 using an access sheath or guide catheter intravascularly inserted via the subclavian vein and superior vena cava. The PTC 20 may be disposed across the atrial septal wall 115 by using transseptal approach similar to that which is used to deliver electrophysiology catheters in the left atrium 117. For example, using fluoroscopic visualization, a guide wire or needle may be used to puncture the septal wall 115, and radiopaque dye may be injected to confirm complete puncture and placement. A dilator and sheath may be advanced over the guide wire to access the left atrium 117. The PSED 400 may then be advanced through the sheath and/or along the guide wire (with the use of a guide wire lumen on the side of the PSED 400), until the PTC 20 extends across the punctured septum 115. The PSED 400 may then be rotated (for a corkscrew-type anchor) or pushed (for a barb-type anchor) to secure the PSED 400 to the septal wall 115.

In this alternative embodiment, the PSED 400 measures blood pressure in the left atrium and generates an electrical pressure signal which is transmitted in analog or digital form to the ITD (ICD or pacemaker) 60 via lead 30. Because rhythm disturbances cause detectable changes in atrial pressure, the pressure measurement signal is indicative of $V_{fib}$ and/or $V_{tach}$ which require a corrective therapeutic stimulus to the heart. Thus, the atrial blood pressure measurement provided by PSED 400 may be used is a similar manner as the pressure measurement provided by PSD 10 described previously.

From the foregoing, it will be apparent to those skilled in the art that the present invention provides, in exemplary nolimiting embodiments, implantable devices that measure vascular pressure, vascular blood flow, tissue perfusion, and/or intracardial pressure, and provide feedback directly to a therapeutic device to improve aberrant rhythm detection. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of internally monitoring a subject and providing, if appropriate, cardiac electrical therapy to the subject, the method comprising:

implanting within the subject a cardiac defibrillator comprising a pulse generator, processing circuitry, and electrodes that are positioned to sense cardiac electrical waveforms and to provide, if needed, cardiac therapy in a form of electrical defibrillation stimulation;

implanting within the subject a pressure sensing device comprising a pressure transmission catheter and a transducer in communication with the pressure transmission catheter, the pressure sensing device being implanted so that a distal sensing tip of the pressure transmission catheter is positioned within an artery accessible in a subcutaneous pectoral region of the chest, but the transducer of the pressure sensing device remains outside of the artery;

receiving, within the implanted cardiac defibrillator, cardiac electrical activity waveform information sensed by the electrodes and pressure waveform information for the artery sensed by the implanted pressure sensor; and providing the cardiac therapy in the form of electrical defibrillation stimulation if the processing circuitry of the implanted cardiac therapeutic device determines that an evaluation of both the cardiac electrical activity waveform information and the pressure waveform information shows there is occurring an aberrant rhythm for which therapy is appropriate.

2. The method of claim 1, wherein at least one of the electrodes is positioned within the heart of the subject, and the sensed electrical activity waveform information is an electrogram signal.

3. The method of claim 1, wherein at least one of the electrodes is positioned subcutaneously within the subject, and the sensed electrical activity waveform information is a subcutaneous electrocardiogram signal.

4. The method of claim 1, wherein the pressure sensing device comprises a lead that has on a first end the pressure transmission catheter and on a second end a connector that is connectable to a housing of the cardiac defibrillator, so that a wired connection between the transducer and the processing circuitry is formed.

5. The method of claim 1, wherein the pressure transmission catheter comprises a lumen extending from the distal tip of the pressure transmission catheter to the transducer.

6. The method of claim 5, wherein the lumen is filled with a pressure transmitting substance providing fluid communication between the distal tip and the transducer.

7. The method of claim 6, wherein the distal tip of the pressure transmission catheter comprises a barrier that retains the substance but that allows external pressure forces to be transmitted through the lumen for detection by the transducer.

8. The method of claim 1, wherein the pressure transmission catheter is an elongate structure that has a diameter that is transverse to a longitudinal axis of the pressure transmission catheter of approximately 0.5 mm to 1.5 mm.

9. The method of claim 1, wherein the artery accessible in a subcutaneous pectoral region is a subclavian artery.

10. The method of claim 1, wherein the determination by the processing circuitry of whether or not to provide the cardiac therapy comprises the use of a likelihood function for both the cardiac electrical activity waveform information and the pressure waveform information to indicate a likelihood that an aberrant rhythm requiring a stimulus is occurring in the heart.

11. The method of claim 10, wherein:

wherein at least one of the electrodes is positioned subcutaneously within the subject, and the sensed electrical activity waveform information is a subcutaneous electrocardiogram (ECG) signal; and if the ECG signal was noisy and thus difficult to interpret, the likelihood function for the cardiac electrical activity waveform information would present a low likelihood that an aberrant rhythm requiring a stimulus is occurring in the heart.

12. The method of claim 1, wherein a presence of an aberrant rhythm from the sensed pressure waveform information is determined from a baseline measurement of pressure and a fall in pressure from the baseline of more than a pre-specified value.

13. A system for internally monitoring a subject and providing, if appropriate, cardiac electrical therapy to the subject, the method comprising:
an implantable cardiac defibrillator comprising a pulse generator, processing circuitry, and electrodes that are positionable to sense cardiac electrical waveforms and to provide, if needed, cardiac therapy in a form of electrical defibrillation stimulation; and
an implantable pressure sensing device comprising a pressure transmission catheter and a transducer in communication with the pressure transmission catheter, the pressure sensing device being implantable so that a distal sensing tip of the pressure transmission catheter is positionable within an artery accessible in a subcutaneous pectoral region of the chest, but the transducer of the pressure sensing device remains outside of the artery;
wherein the implantable cardiac defibrillator is programmed to receive cardiac electrical activity waveform information sensed by the electrodes and pressure waveform information for the artery sensed by the implantable pressure sensor, and is further programmed to direct that cardiac therapy be provided in the form of electrical defibrillation stimulation if the processing circuitry determines that an evaluation of both the cardiac electrical activity waveform information and the pressure waveform information shows there is occurring an aberrant rhythm for which therapy is appropriate.

14. The system of claim 13, wherein:
the cardiac defibrillator comprises at least one endocardial lead having a distal electrode positionable within the heart of the subject; and
the processing circuitry is programmed to analyze sensed electrical activity waveform information in a form of an electrogram signal that is sensed by the at least one endocardial lead electrode.

15. The system of claim 13, wherein:
the cardiac defibrillator comprises at least one subcutaneous electrode positionable subcutaneously within the subject; and
the processing circuitry is programmed to analyze sensed electrical activity waveform information in the form of a subcutaneous electrocardiogram signal that is sensed by the at least one subcutaneous electrode.

16. The system of claim 13, wherein the pressure sensing device comprises a lead that has on a first end the pressure transmission catheter and on a second end a connector that is connectable to a housing of the cardiac defibrillator, so that a wired connection between the transducer and the processing circuitry is formable.

17. The system of claim 13, wherein the pressure transmission catheter comprises a lumen extending from the distal tip of the pressure transmission catheter to the transducer.

18. The system of claim 17, wherein the lumen is filled with a pressure transmitting substance providing fluid communication between the distal tip and the transducer.

19. The system of claim 18, wherein the distal tip of the pressure transmission catheter comprises a barrier that retains the substance but that allows external pressure forces to be transmitted through the lumen for detection by the transducer.

20. The system of claim 13, wherein the pressure transmission catheter is an elongate structure that has a diameter that is transverse to a longitudinal axis of the pressure transmission catheter of approximately 0.5 mm to 1.5 mm.

21. The system of claim 13, wherein the processing circuitry is programmed to determine whether or not to provide the cardiac therapy using a likelihood function for both the cardiac electrical activity waveform information and the pressure waveform information to indicate a likelihood that an aberrant rhythm requiring a stimulus is occurring in the heart.

22. The system of claim 21, wherein:
at least one of the electrodes is a subcutaneous electrode positionable in a subcutaneous region of the subject;
the processing circuitry is programmed to interpret sensed electrical activity waveform information in a form of a subcutaneous electrocardiogram (ECG) signal; and
the processing circuitry is further programmed such that if the ECG signal was noisy and difficult to interpret, the likelihood function for the cardiac electrical activity waveform information would present a low likelihood that an aberrant rhythm requiring a stimulus is occurring in the heart.

23. The system of claim 13, wherein the processing circuitry is programmed such that a presence of an aberrant rhythm from the sensed pressure waveform information is determined from a baseline measurement of pressure and a fall in pressure from the baseline of more than a pre-specified value.

* * * * *

UNITED STATES PATENT AND TRADEMARK OFFICE
CERTIFICATE OF CORRECTION

PATENT NO.         : 7,529,583 B1
APPLICATION NO.    : 10/756188
DATED              : May 5, 2009
INVENTOR(S)        : Brockway et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (266) days Delete the phrase "by 266 days" and insert -- by 217 days --

Signed and Sealed this

Thirteenth Day of October, 2009

David J. Kappos
*Director of the United States Patent and Trademark Office*